US006969451B2

(12) United States Patent
Shin et al.

(10) Patent No.: US 6,969,451 B2
(45) Date of Patent: Nov. 29, 2005

(54) FLUID-TYPE MULTIPLE ELECTROCHEMICAL SYSTEM AND PREPARATION THEREOF

(75) Inventors: Dong-Ho Shin, Daejon (KR); Sun Kil Kang, Gyeonggi-Do (KR); Hyokyum Kim, Daejon (KR); Haesik Yang, Daejon (KR); Youn Tae Kim, Daejon (KR)

(73) Assignee: Electronics and Telecommunications Research Institute, (KR)

( * ) Notice: Subject to any disclaimer, the term of this patent is extended or adjusted under 35 U.S.C. 154(b) by 466 days.

(21) Appl. No.: 10/334,553

(22) Filed: Dec. 30, 2002

(65) Prior Publication Data

US 2004/0084306 A1 May 6, 2004

(30) Foreign Application Priority Data

Oct. 30, 2002 (KR) ............... 10-2002-0066611

(51) Int. Cl.[7] ............... G01N 27/403; G01N 27/31; C25B 3/00
(52) U.S. Cl. ............... 204/412; 204/269; 205/414; 205/422; 205/423; 205/424; 205/425; 205/426; 205/427; 205/428
(58) Field of Search ............... 204/403.01–403.14, 204/409, 411, 412, 269; 205/413, 414, 422–428, 205/440–443

(56) References Cited

U.S. PATENT DOCUMENTS

| 6,123,820 A | * | 9/2000 | Bergkuist et al. ........... 204/411 |
| 6,187,164 B1 | | 2/2001 | Warren et al. |
| 6,340,421 B1 | | 1/2002 | Vachon et al. |

OTHER PUBLICATIONS

Anal. Chem. 2002, 74, 355-361, "Immobilization Method for the Preparation of Biosensors . . . ", C. Kurzawa, et al., 7 pages.

* cited by examiner

Primary Examiner—Alex Noguerola
(74) Attorney, Agent, or Firm—Blakely, Sokoloff, Taylor & Zafman

(57) ABSTRACT

A fluid-type multiple electrochemical system. The system includes a substrate for an electric circuit having a plurality of electrode parts formed at regular intervals. The electrode parts each include a reference electrode and an auxiliary electrode. Also provided is a fluid-type substrate having a fluid injection part, a fluid ejection part and a plurality of fluid storages. The fluid storages are formed at the same regular intervals as the electrode parts of the substrate and are connected with each other through fluid passages. The system also includes a sensor substrate having a plurality of unit sensors formed at the same regular intervals as the electrode parts of the substrate. Each unit sensor has an electrode part, an electrode pad for supplying power voltage simultaneously, and an electrode wiring.

9 Claims, 4 Drawing Sheets

FLUID-TYPE MULTIPLE ELECTROCHEMICAL SYSTEM AND PREPARATION THEREOF

FIELD OF THE INVENTION

The present invention relates to a fluid-type multiple electrochemical system to be applied to a biosensor manufacturing process; and, more particularly, to a fluid-type multiple electrochemical system that performs the process of forming an internal layer or an enzyme layer on an electrode array formed on a substrate collectively by using a fluid having a simple structure.

DESCRIPTION OF RELATED ART

An enzyme electrode sensor means a biological sensor that can be used for determining the concentration of a certain biochemical material quickly and relatively precisely. Enzyme electrode sensors are generally used to detect glucose, urea, uric acid and various alcohols. For example, a glucose sensor has a glucose-sensitive enzyme, such as glucose oxidase, deposited on the surface of an electrode. This enzyme layer is prepared and deposited by dipping a substrate in an electrolyte solution, such as protein stabilizer, monomer or PBS, to which a glucose oxidase is added, and inducing an electrochemical reaction between the substrate and the electrolyte solution.

This method of depositing an enzyme layer requires a considerable amount of the electrolyte solution to dip the electric substrate entirely. Also, if there is an array of electrodes, it may lead to the protein contamination of an auxiliary electrode or a reference electrode. As this process is repeated, the concentration of the components in the electrode solution becomes lower, thus dropping the reproducibility of the enzyme layer deposition.

Accordingly, required is an improved method that can secure high efficiency and reproducibility of an enzyme layer preparation and provide an electrochemical process suitable for process automation.

To solve the above problem, U.S. Pat. No. 6,340,421 B1 discloses 'Microelectrogravimetric Method for Plating a Biosensor,' registered on Jan. 22, 2002. The patent suggests a method for forming an enzyme layer by dropping droplets of an electrolyte solution on the surface of an electrode using a micro-dispenser and thereby forming an electrochemical system between the tip of the dispenser, electrodes and the droplets of the electrolyte. This method has advantages that the cost for manufacturing a sensor is reduced, and the enzyme layer is formed reproducibly, as well as protecting electrodes from contamination. However, using the micro-dispenser causes some problems.

In the first, when an enzyme layer is deposited on several sensors simultaneously, time is consumed as much as the number of sensors formed on the electrode substrate, because the one-dimensional micro dispenser array should move as much as the electrode array and perform the electrochemical deposition.

Secondly, when various enzyme layers are formed on one sensor, the work should be carried out separately by applying an enzyme layer and changing the micro-dispenser with new one or cleaning it, and then applying another one.

Lastly, the automated equipment, such as the micro-dispenser, is expensive, and when many dispensers should be used, a potentiometer should be added thereto to drive and control the dispensers. So, the overall system becomes very complicated and it requires high cost.

SUMMARY OF THE INVENTION

It is, therefore, an object of the present invention to provide a fluid-type electrochemical system, and a method for preparing the fluid-type electrochemical system in order to solve the problems described above.

The present invention provides a fluid-type multiple electrochemical system which sends an electrolyte to designated locations with the help of a fluid device, which is composed of flexible polymers, to connect the locations with the electrolyte so that an electrochemical reaction could be incurred in all electrodes simultaneously.

In accordance with an aspect of the present invention, there is provided a fluid-type multiple electrochemical system having an electric circuit embodied in a substrate, a fluid-type substrate and a sensor substrate, and a preparation method thereof, the substrates being combined to form an electrochemical system.

In accordance with an aspect of the present invention, there is provided a fluid-type multiple electrochemical system, comprising: a substrate for an electric circuit, which includes a plurality of electrode parts formed at regular intervals, the electrode part having a reference electrode and an auxiliary electrode; a fluid-type substrate having a fluid injection part, a fluid ejection part and a plurality of fluid storages, the fluid storages being formed at the same interval as the electrode part of the substrate for an electric circuit, and connected with each other through fluid passages; and a sensor substrate having a plurality of unit sensors formed at the same interval as the electrode part of the substrate for an electric circuit, each unit sensor being composed of an electrode part, an electrode pad for supplying power voltage simultaneously, and an electrode wiring.

In accordance with another aspect of the present invention, there is provided a method for preparing a fluid-type multiple electrochemical system having a substrate for an electric circuit, a fluid-type substrate and a sensor substrate, comprising the steps of: a) forming a plurality of electrode parts having a reference electrode and an auxiliary electrode on the substrate for an electric circuit at regular intervals; b) forming a fluid injection part and a fluid ejection part on one side of the fluid-type substrate, forming a plurality of fluid storages at the same interval as the electrode parts formed on the substrate for an electric circuit, and forming fluid passages for connecting the fluid storages with each other; and c) forming a plurality of unit sensors on the sensor substrate at the same interval as the electrode parts formed on the substrate for an electric circuit, the unit sensor including an electrode part having a reference electrode, an auxiliary electrode and a working electrode, an electrode pad and an electrode wiring.

In accordance with an aspect of the present invention, the electrode pads are connected with each other so that power or power voltage could be supplied to the electrodes on the substrate for an electric circuit and the sensor substrate, simultaneously.

In accordance with an aspect of the present invention, the fluid retained in the fluid storages of the fluid-type substrate contacts the electrode parts of the sensor substrate to form a plurality of electrochemical systems so as to perform an electrochemical reaction, simultaneously.

In accordance with an aspect of the present invention, a protective layer is formed on top of the reference electrodes and auxiliary electrodes of the sensor substrate.

In accordance with an aspect of the present invention, the protective layer is a hydrogel selected from a group consisting of polyvinyl alcohol (PVA), polyacrylamide (PAAM), poly N-vinyl pyrrolidone (PNVP), polyhydroxyethyl methacrylate (PHEMA), polyethylene glycol (PEG), polyethylene oxide (PEO), polyethylene glycol monomethyl ether (PEGME) and cellulose.

BRIEF DESCRIPTION OF THE DRAWINGS

The above and other objects and features of the present invention will become apparent from the following description of the preferred embodiments given in conjunction with the accompanying drawings, in which.

DETAILED DESCRIPTION OF THE INVENTION

Other objects and aspects of the invention will become apparent from the following description of the embodiments with reference to the accompanying drawings, which is set forth hereinafter.

Figure 1:
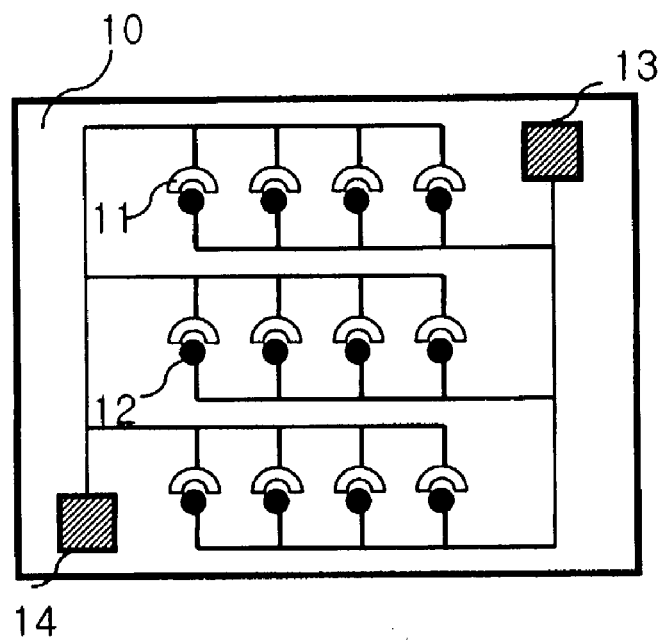
FIG. 1 is a plane figure showing a substrate for an electric circuit in a fluid-type multiple electrochemical system in accordance with an embodiment of the present invention.

FIG. 1 is a plane figure showing a substrate 10 for an electric circuit in a fluid-type multiple electrochemical system in accordance with an embodiment of the present invention. The substrate 10 for an electric circuit includes arrays of a reference electrode 11 and an auxiliary electrode 12 formed thereon at regular intervals. Each electrode array is connected to each other to be driven collectively. The reference electrode 11 and the auxiliary electrode 12 are needed for an electrochemical reaction.

The substrate 10 for the electric circuit can be made of silicon, glass or polymer. On the substrate, the reference electrodes 11 and the auxiliary electrodes 12 are formed in such a method as electroplating, E-beam, sputtering or screen printing. Here, Ag/AgCl or IrO$_2$ is used for forming the reference electrode 11. For the auxiliary electrodes 12, Pt may be used.

Figure 2:
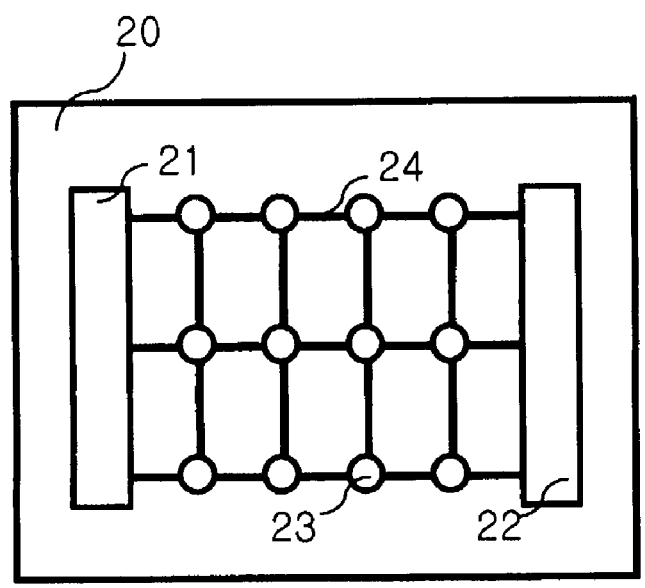
FIG. 2 is a plane figure illustrating a fluid-type substrate of the fluid-type multiple electrochemical system in accordance with the embodiment of the present invention.

FIG. 2 is a plane figure illustrating a fluid-type substrate 20 of the fluid-type multiple electrochemical system in accordance with the embodiment of the present invention. On the fluid-type substrate 20, grooves and holes are formed at regular intervals to form fluid storages 23 and fluid passages 24 for connecting the fluid storages 23. On one side of the fluid-type substrate 20, a fluid injection chamber 21 and a fluid ejection chamber 22 are formed. The fluid-type substrate 20 may include an additional reference and auxiliary electrodes on one side.

The fluid-type substrate 20 may be formed of various kinds of polymer, such as polymethyl methacrylate (PMMA), polycarbonate (PC), cycloolefin copolymer (COC), polydimethylsiloxane (PDMS), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP) and perfluoralkoxyalkane (PFA). The fluid-type substrate 20 is formed by using a traditional machining method, such as hot embossing, injection molding, casting, stereolithography, laser ablation, rapid prototyping, silk screening and numerical control (NC) machining, or using semiconductor processing, such as deposition and etching.

Figure 3:
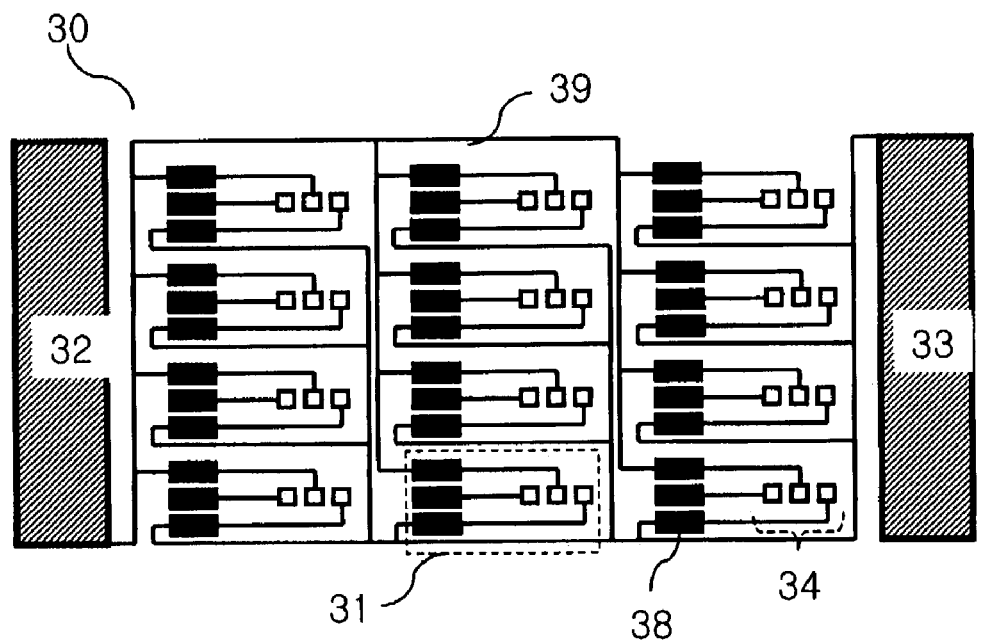
FIG. 3 is a plane figure describing a sensor substrate of the fluid-type multiple electrochemical system in accordance with the embodiment of the present invention.

FIG. 3 is a plane figure describing a sensor substrate 30 of the fluid-type multiple electrochemical system in accordance with the embodiment of the present invention. On the sensor substrate 30, unit sensors are arrayed. Each unit sensor is composed of an electrode 34, an electrode pad 38 and an electrode wiring 39. The sensor substrate 30 is connected with big electrode pads 32 and 33 through the electrode wiring 39. The sensor substrate can be formed of such flexible polymer as silicon wafer, polyimide (PI) or liquid crystalline polymer (LCP). For the fabrication of the sensor array, traditional semiconductor processing methods can be used.

Figure 4:
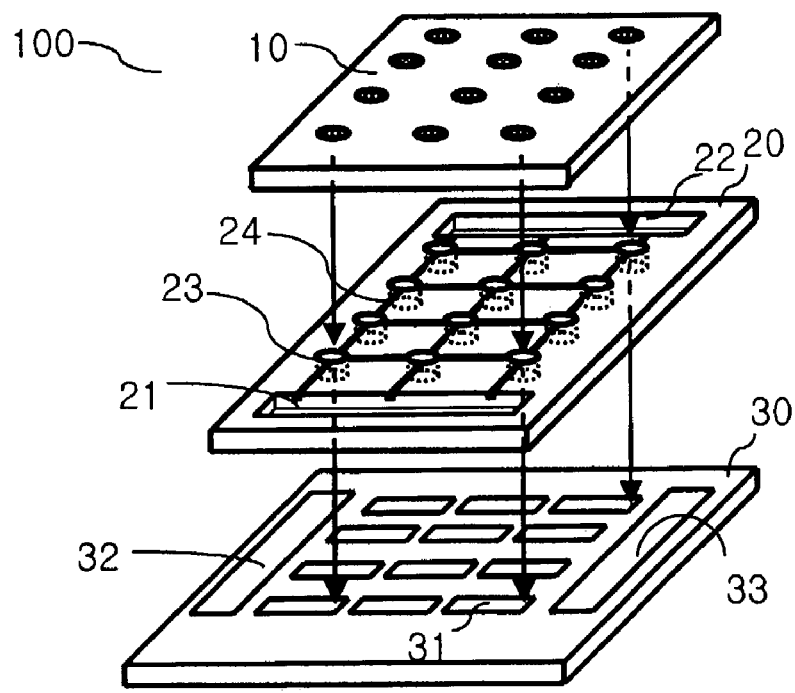
FIG. 4 is a diagram showing how the substrates are combined in the fluid-type multiple electrochemical system in accordance with the embodiment of the present invention.

FIG. 4 is a diagram showing how the substrates, i.e., the substrate 10 for an electric circuit of FIG. 1, the fluid-type substrate 20 of FIG. 2 and the sensor substrate 30 of FIG. 3, are combined in the fluid-type multiple electrochemical system in accordance with the embodiment of the present invention. The fluid-type multiple electrochemical system 100 of the present invention is completed by combining the fluid-type substrate 20 and the substrate 10 for an electric circuit on the sensor substrate 30 sequentially.

First, fluid storages 23 are positioned on top of the electrode parts 34 of the sensor substrate 30. Then, electrolyte is injected to a fluid injection chamber 21. The injected electrolyte is flown to a fluid ejection chamber 22 along the fluid passages passing through the fluid storages 23. Subsequently, the substrate 10 for an electric circuit is mounted on top of the fluid-type substrate 20. Here, the portion where the reference electrode 11 and the auxiliary electrode 12 are laid is positioned perpendicularly to the electrode parts 34 of the sensor substrate 30. By doing so, each fluid storage forms a single electrochemical system, and the electrochemical systems are connected with each other through the electrolyte to incur multiple electrochemical reactions, simultaneously.

More characteristic functions of the present invention will be described herein, taking a preparation example, in which an enzyme can be immobilized in the electrochemical method by using the electrochemical system of the present invention.

Formation of Protective Layer

Figure 5A:
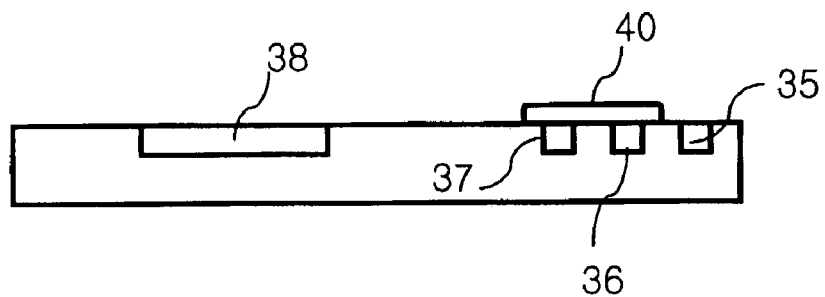
FIG. 5A is a cross-sectional view illustrating a protective layer formed on top of a reference electrode and an auxiliary electrode.

In the enzyme immobilization process, if the reference electrode and the auxiliary electrode formed on the sensor substrate 30 contacts such protein as glucose oxidase, the protein may be adsorbed on the surface of the electrodes, thus contaminating the electrodes. In consideration of this point, a protective layer is deposited on the reference electrode and the auxiliary electrode prior to the reaction to protect the electrodes from protein contamination, as shown in FIG. 5A.

The protective layer can be formed on one component of the biosensor by performing spin-coating or tip-coating, and then performing optical-etching, or by carrying out screen printing. Desirably, the protective layer is formed of a water-soluble polymer that can be removed easily after the formation of an enzyme layer. In case where the protective layer and the exterior layer of the sensor are formed of the same material, the protective layer needs not be removed. Materials for the protective layer is a living body-friendly hydrogel material, such as polyvinyl alcohol (PVA), polyacrylamide (PAAM), poly N-vinyl pyrrolidone (PNVP), polyhydroxyethyl methacrylate (PHMEMA), polyethylene glycol (PEG), polyethylene oxide (PEO), polyethylene glycol monomethyl ether (PEGME), and cellulose.

Combination of Substrates

Figure 5B:
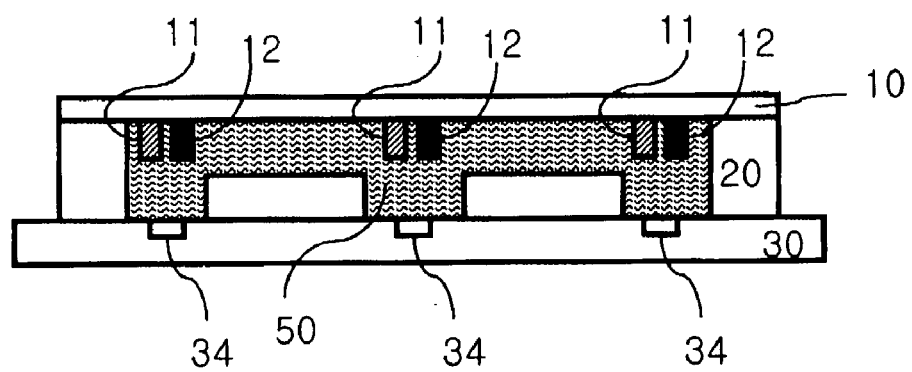
FIGS. 5B and 5C are cross-sectional views at different angles describing the substrates of the fluid-type multiple electrochemical system to form an electrochemical system in accordance with the embodiment of the present invention.
Figure 5C:
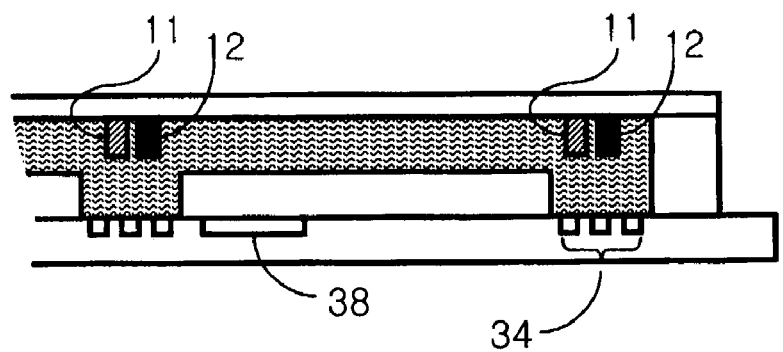

The fluid-type substrate 20 is mounted on top of the sensor substrate 30. Here, the electrode parts of the sensor come in contact with the fluid storage part of the fluid-type substrate 20 (see FIGS. 5B and 5C). A solution prepared by mixing an enzyme and monomer (for example, 1,3-phenylenediamine), which is not polymerized yet, in an appropriate ratio is injected to the fluid-type injection chamber 21 and filled in the fluid storages 23 through the fluid passages 24 formed on the fluid-type substrate 20.

The substrate 10 for an electric circuit is mounted on top of the fluid-type substrate 20. The reference electrode 11 and the auxiliary electrode 12 are mounted perpendicularly to the electrode part 34 of the sensor 31 and the fluid storages 23 so that all of them could form an electrochemical system (see FIGS. 5B and 5C).

The big electric pads and the electric pads 13 and 14 of the substrate for an electric circuit are connected with an external potentiometer to incur an electrochemical reaction.

When the above processes are completed, the same enzyme layer is formed on all the sensors 31 and the working electrodes 35 simultaneously. In this invention, the electrochemical reaction may be induced in a method of dipping an additional reference electrode and auxiliary electrode in the fluid injection chamber 21 or the fluid ejection chamber 22 of the fluid-type substrate 20, instead of the substrate 10 for an electric circuit, which is mounted on the fluid-type substrate 20.

Figure 6:
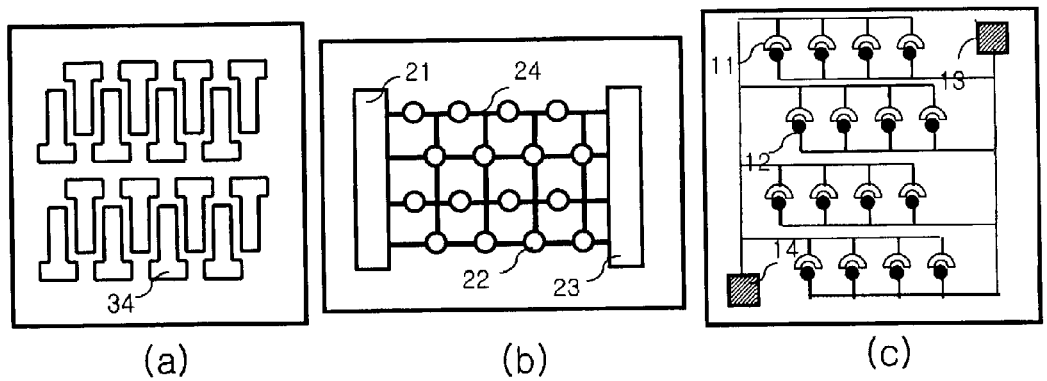
FIGS. 6 and 7 are plane figures showing diverse electrode arrays of the fluid-type multiple electrochemical system in accordance with the embodiment of the present invention.
Figure 7:
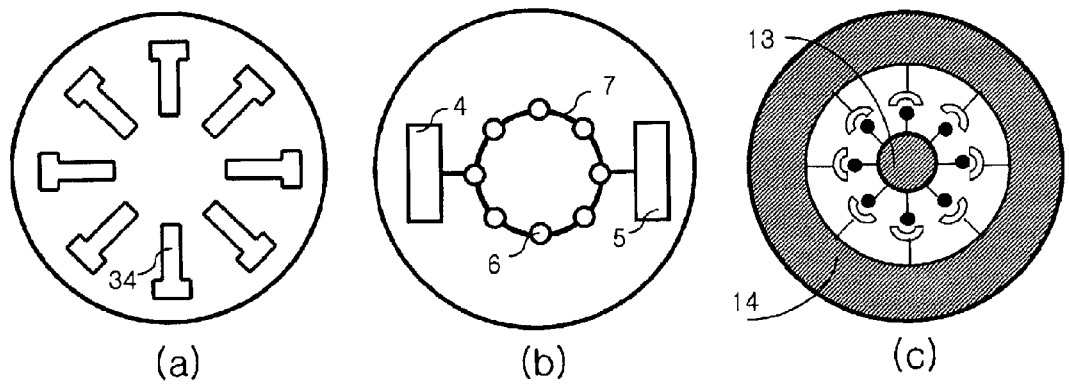

FIGS. 6 and 7 are plane figures showing the fluid-type substrate 20 and the substrate 10 for an electric circuit 10, which have diverse array forms, in the fluid-type multiple electrochemical system in accordance with the embodiment of the present invention. Depending on the integration or usage, the sensor substrate 30 may be formed with the sensors arrayed in a line, crossed over with each other, or radiated. From the drawings, it can be seen that the fluid-type substrate 20 and the substrate 10 for an electric circuit 10 have an advantage that they can be fabricated suitably for the array of the sensor substrate 30.

As described above, the system of the present invention can be applied to a biosensor fabrication process that forms an enzyme layer on all the electrodes formed on the sensor substrate 30, simultaneously, by forming a multiple electrochemical system. The multiple electrochemical system is formed by injecting the electrolyte 50 to the electrode part 34 at a predetermined location of the top of the sensor substrate 30, and mounting the fluid-type substrate 20 which connects the electrode parts 34 with each other through the electrolyte 50, and providing the substrate 10 for an electric circuit having the reference electrode 11 and the auxiliary electrode 12 arrayed on the fluid-type substrate 20. The reference electrode 11 and the auxiliary electrode 12 are constituents of the electrochemical system.

As described above, the fluid-type multiple electrochemical system of the present invention can solve the problems the conventional systems have, such as consumption of electrolyte, protein contamination, and degrading reproducibility of sensors, effectively.

While the present invention has been described with respect to certain preferred embodiments, it will be apparent to those skilled in the art that various changes and modifications may be made without departing from the scope of the invention as defined in the following claims.

What is claimed is:

1. A fluid-type multiple electrochemical system, comprising:
   a substrate for an electric circuit, which includes a plurality of electrode parts formed at regular intervals, each electrode part having a reference electrode and an auxiliary electrode;
   a fluid-type substrate having a fluid injection part, a fluid ejection part and a plurality of fluid storages, the fluid storages being formed at the same regular intervals as the electrode parts of the substrate for an electric circuit, and connected with each other through fluid passages; and
   a sensor substrate having a plurality of unit sensors formed at the same each intervals as the electrode part of the substrate for an electric circuit, each unit sensor being composed of an electrode part, an electrode pad for supplying power voltage simultaneously, and an electrode wiring.

2. The system as recited in claim 1, wherein the electrode part of the sensor substrate includes a reference electrode, an auxiliary electrode, and a working electrode, and a protective layer is deposited on top of the reference and the auxiliary electrodes among the three electrodes.

3. The system as recited in claim 2, wherein the protective layer is a hydrogel selected from a group consisting of polyvinyl alcohol (PVA), polyacrylamide (PAAM), poly N-vinyl pyrrolidone (PNVP), polyhydroxyethyl methacrylate (PHEMA), polyethylene glycol (PEG), polyethylene oxide (PEO), polyethylene glycol monomethyl ether (PEGME) and cellulose.

4. The system as recited in claim 1, wherein an additional reference electrode and auxiliary electrode are inserted in a fluid injection part or a fluid ejection part of the fluid-type substrate.

5. A method for preparing a fluid-type multiple electrochemical system having a substrate for an electric circuit, a fluid-type substrate, and a sensor substrate, comprising the steps of:
   a) forming a plurality of electrode parts each having a reference electrode and an auxiliary electrode on the substrate for an electric circuit at regular intervals;
   b) forming a fluid injection part and a fluid ejection part on one side of the fluid-type substrate, forming a plurality of fluid storages at the same intervals as the electrode parts formed on the substrate for an electric circuit, and forming fluid passages for connecting the fluid storages with each other; and
   c) forming a plurality of unit sensors on the sensor substrate at the same intervals as the electrode parts formed on each substrate for an electric circuit, the unit sensor including an electrode part having a reference electrode, an auxiliary electrode and a working electrode, an electrode pad and an electrode wiring.

6. The method as recited in claim 5, wherein the electrode pads are connected with each other so that power or power voltage could be supplied to the electrodes on the substrate for an electric circuit and the sensor substrate, simultaneously.

7. The method as recited in claim 5, wherein the fluid retained in the fluid storages of the fluid-type substrate contacts the electrode parts of the sensor substrate to form a plurality of electrochemical systems so as to perform an electrochemical reaction, simultaneously.

8. The method as recited in claim 5, wherein a protective layer is formed on top of the reference electrodes and auxiliary electrodes of the sensor substrate.

9. The method as recited in claim 8, wherein the protective layer is a hydrogel selected from a group consisting of polyvinyl alcohol (PVA), polyacrylamide (PAAM), poly N-vinyl pyrrolidone (PNVP), polyhydroxyethyl methacrylate (PHEMA), polyethylene glycol (PEG), polyethylene oxide (PEO), polyethylene glycol monomethyl ether (PEGME) and cellulose.

* * * * *